United States Patent
Lang et al.

(10) Patent No.: US 7,727,481 B2
(45) Date of Patent: Jun. 1, 2010

(54) SPECIMEN HOLDER HAVING AN INSERT FOR ATOMIC FORCE MICROSCOPY

(75) Inventors: Anton Lang, Vienna (AT); Rainer Wogritsch, Vienna (AT); Andreas Nowak, Vienna (AT)

(73) Assignee: Leica Mikrosysteme GmbH, Vienna (AT)

( * ) Notice: Subject to any disclaimer, the term of this patent is extended or adjusted under 35 U.S.C. 154(b) by 1088 days.

(21) Appl. No.: 10/732,076

(22) Filed: Dec. 10, 2003

(65) Prior Publication Data

US 2004/0120862 A1 Jun. 24, 2004

(30) Foreign Application Priority Data

Dec. 11, 2002 (DE) ................................ 102 58 104

(51) Int. Cl.
*G01N 1/06* (2006.01)

(52) U.S. Cl. ................. 422/104; 422/99; 83/915.5; 435/40.52; 436/174; 436/176

(58) Field of Classification Search ................ 220/230; 83/915.5; 422/99, 104; 435/40.52; 436/174, 436/176

See application file for complete search history.

(56) References Cited

U.S. PATENT DOCUMENTS

| | | | | |
|---|---|---|---|---|
| 2,155,523 A * | 4/1939 | Bausch et al. | ................. | 83/416 |
| 3,940,219 A * | 2/1976 | Pickett et al. | ............... | 425/117 |
| 4,045,291 A * | 8/1977 | Berger | ..................... | 435/297.5 |
| 4,150,593 A * | 4/1979 | Butler | ........................... | 83/42 |
| 4,596,934 A | 6/1986 | Yanaka et al. | | |
| 4,805,443 A * | 2/1989 | Schroeder | ...................... | 73/37 |
| 5,253,516 A | 10/1993 | Elings et al. | .................. | 73/105 |
| 5,270,010 A * | 12/1993 | Lautenschlager | ........... | 422/102 |
| 6,414,322 B1 * | 7/2002 | Carroll | .................. | 250/442.11 |
| 2002/0005492 A1 * | 1/2002 | Hashikawa et al. | .... | 250/442.11 |

FOREIGN PATENT DOCUMENTS

| | | |
|---|---|---|
| DE | 19918078 | 10/1999 |
| GB | 1190944 | 5/1970 |
| JP | 06186027 A | 7/1994 |

OTHER PUBLICATIONS

Y. Thomann, R. Thomann, G. Bar, M. Ganter, B. Machutta & R. Muelhaupt, "Combined ultramicrotomy for AFM and TEM using a novel sample holder", Journal of Microscopy, vol. 195, Pt. 2, Aug. 1999, pp. 161-163.
Journal of Microscopy, "Combined ultramicrotomy for AFM and TEM using a novel sample holder", vol. 195, Pt. 2, Aug. 1999, pp. 161-163.

* cited by examiner

*Primary Examiner*—Jill Warden
*Assistant Examiner*—Paul S Hyun
(74) *Attorney, Agent, or Firm*—Simpson & Simpson, PLLC

(57) ABSTRACT

A specimen holder (10) is proposed in order to create a capability for preparing, in a cutting device, in particular a microtome or ultramicrotome, a specimen that is to examined in an AFM. The specimen holder (10) is embodied in several parts. It comprises an insert (12) in which the specimen is secured. Also provided is a receiving ring (14) in which the insert (12) can be received. The insert together with the receiving ring (14) is mounted, in particular thread-joined, on a base element (16). As a result of the mounting of the receiving ring (14) on the base element (16), the insert together with the specimen is fixed in its position.

10 Claims, 2 Drawing Sheets

SPECIMEN HOLDER HAVING AN INSERT FOR ATOMIC FORCE MICROSCOPY

CROSS REFERENCE TO RELATED APPLICATIONS

This application claims priority of the German patent application 102 58 104.5 which is incorporated by reference herein.

FIELD OF THE INVENTION

The invention concerns a specimen holder for a microtome or ultramicrotome.

BACKGROUND OF THE INVENTION

A wide variety of capabilities are available, in principle, for the examination of specimens. Particularly popular in this context are, among others, transmission electron microscopy and atomic force microscopy (AFM). One possibility for examining a specimen using an AFM is known, for example, from U.S. Pat. No. 5,253,516. Here the specimen is immobilized in a specimen holder and scanned by a scanning tip. The signals acquired via the scanning tip are electronically converted into an image of the surface of the specimen.

The surface of the specimen is often cut into in order to prepare the surface. Microtomes or ultramicrotomes, for example, can be used for this purpose. These methods, which are known originally from the production of thin sections for TEM examination, can also be successfully used here. It is not necessary, however, to produce thin sections in order to prepare the specimen for AFM examination. The emphasis here, instead, is on preparing the surface of the specimen by way of an exact cut so as to produce a smooth, flat surface. The reason is that specimens to be examined in an AFM must essentially meet two criteria. They must on the one hand have a flat surface which, on the other hand, must be arranged parallel to the surface of a piezoelement on which the sample is mounted. But when a flat surface is produced in a microtome or ultramicrotome and the specimen is removed from the microtome or ultramicrotome mount after cutting, it is practically impossible to arrange that surface once again parallel to the piezoelectric crystal of the AFM.

To circumvent these difficulties, a specimen holder that can be used in a cutting device such as a microtome or ultramicrotome has already been proposed in the article in "Journal of Microscopy" Vol. 195, Pt. 2, August 1999, pp. 161-163. The specimen holder has a central region in which the sample is secured. This central region is removed from the holder of the microtome or ultramicrotome after cutting, and has a flat surface. The central region of the specimen holder is then secured, together with the specimen, on the surface of a specimen stage close to the tip of an AFM. The tip scans the surface of the specimen by means of a piezoelement. Inside the cutting device, the specimen holder is secured with the aid of three screws that must be loosened again for removal of the central insert. In the context of cutting in a refrigeration chamber, which is necessary for many biological or plastic specimens, removal is difficult or impossible. The reason is that the specimen holder must be rotated to the positions of the individual screws. The insert must not fall out when the last screw is loosened, since otherwise the surface could be touched or destroyed. In addition, the insert can be damaged upon removal from a refrigerated chamber, or ambient atmospheric moisture can condense on the surface of the specimen. This, however, renders the sample element unusable for AFM examination.

SUMMARY OF THE INVENTION

The object of the present invention is correspondingly to propose a specimen holder for the examination of specimens in an AFM that is usable in a cutting device such as an ultramicrotome or microtome, and that can easily be removed.

This object is achieved, according to the present invention, by a specimen holder comprising an insert for holding a specimen, a base element, a receiving ring for a releasable reception of the insert and the receiving ring being releasably connected to the base element and the receiving ring comprises has a slot for the reception of the insert.

According to the present invention, the specimen is thus constructed in several parts. It comprises an insert in which the specimen can be secured. The insert can be connected to a receiving ring. The receiving ring is then mounted, together with the insert, on a base element. Advantageously, the insert is thread-joined to the base element in such a way that the insert is secured in clamping fashion. For that purpose, the receiving ring is advantageously embodied as a screw-on ring that has a lateral slot, so that the insert can easily be introduced into the receiving ring. With a three-part embodiment of this kind it is possible to mount the insert, together with the specimen, in the base element in such a way that there is no need to secure the insert directly using screws. Since it is very easy to move the receiving ring into a position in which the insert can be removed, the insert can be removed particularly quickly.

The specimen holder according to the present invention can advantageously be enhanced by the fact that a cover, which can be used as an aid to removal of the insert, is additionally provided. The cover is embodied in such a way that it can be connected in the simplest possible fashion to the insert, and the insert can thus be easily removed from the receiving ring with the aid of the cover. In addition to usual closure technologies such as bayonet closures, magnets are particularly suitable for easy connection, these being provided either on the insert itself or preferably on the cover. If the magnets are provided on the cover, the insert—which in this case must be produced from a material that adheres to a magnet—can be easily removed. The cover usually comprises a cavity in which the sample can be received without being damaged. The cover is particularly suitable for transferring the insert, together with the specimen secured in the insert, out of the refrigerated chamber of an ultramicrotome. Undesired effects such as, for example, the condensation of water on the sample surface can thereby be prevented. In addition, the insert can be embodied in such a way that manipulation aids, with which it is possible to manipulate the insert during mounting and removal, can be provided.

The insert itself is embodied and shaped so that it can easily be mounted in an AFM, advantageously directly on the piezo-element used in the AFM. Use of the specimen holder in an AFM has the decisive advantage that the insert can be introduced into the AFM together with the specimen, which is secured therein and has been trimmed at its surface by means of the microtome. Examination of the specimen with the AFM can begin immediately, without removing the specimen from the insert or modifying its alignment with respect to the surface to be examined.

BRIEF DESCRIPTION OF THE DRAWINGS

Further advantages and advantageous embodiments of the invention are the subject matter of the Figure descriptions below.

In the individual Figures.

DETAILED DESCRIPTION OF THE INVENTION

Figure 1:
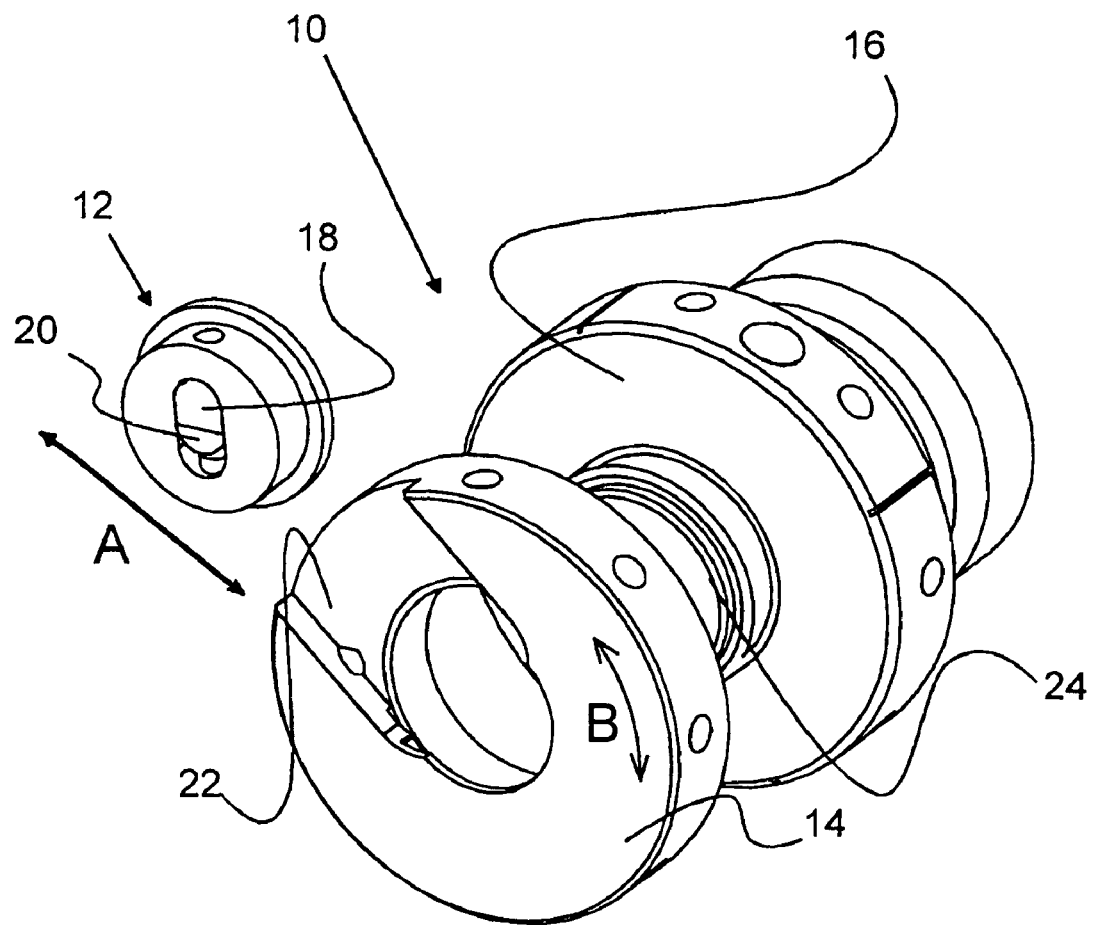
FIG. 1 shows a specimen holder according to the present invention, having an insert, a receiving ring, and a base element.

FIG. 1 is a perspective depiction of a specimen holder according to the present invention. The specimen holder comprises an insert 12 in which a specimen can be secured. The specimen is secured by clamping the specimen between the two clamping jaws 18 and 20. The insert itself is dimensioned and shaped in such a way that it can be used as a specimen holder in an AFM.

After the specimen has been secured in insert 12, insert 12 can be received in a receiving ring 14. As shown in FIG. 1, reception in receiving ring 14 is preferably accomplished by the fact that a slot 22 adapted to the dimension of insert 12 is provided in receiving ring 14. Insert 12 can thus be introduced into the receiving ring, and removed again therefrom, in arrow direction A. A securing device, for example a spring-loaded clamping ball, can additionally be provided for securing insert 12 in receiving ring 14.

After the introduction of insert 12 into receiving ring 14, receiving ring 14 is connected to base element 16 of specimen holder 10. This is preferably accomplished by thread-joining receiving ring 14 to thread 24 of base element 16. Base element 16 and receiving ring 14 are preferably matched to one another for this purpose in such a way that a relatively small rotation, for example a quarter-turn, of receiving ring 14 is already sufficient to secure insert 12 by clamping. For the introduction and removal of insert 12, base element 16 is advantageously rotated in such a way that the slot of the screw-on ring points upward and insert 12 can thus be removed safely, the rotation occurring in arrow direction B.

Figure 2:
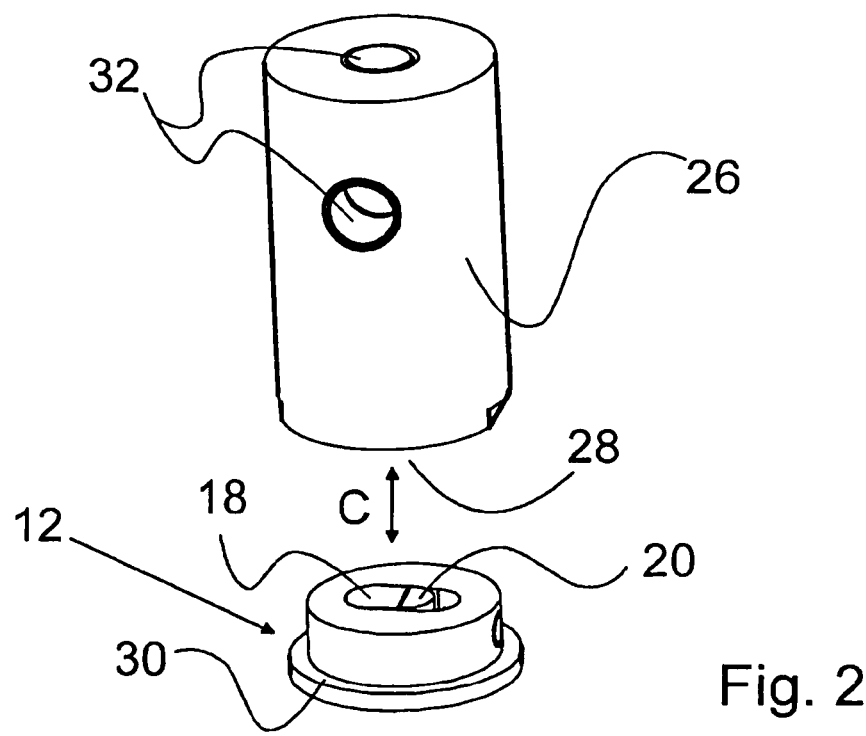
FIG. 2 shows an insert with a cover located thereabove.

As shown in FIG. 2, in a further advantageous embodiment of the invention a cover 26 can additionally be provided. Cover 26 is embodied in such a way that insert 12 can be completely covered by it. Bottom 28 of cover 26 is adapted to the shape of insert 12 in such a way that it can be supported on ring 30 of insert 12.

Securing means 34, with which an immovable connection between insert 12 and cover 26 can be achieved, can be provided for securing cover 26 on insert 12. These securing means 34 can be mounted both on insert 12 and on cover 26.

Figure 3:
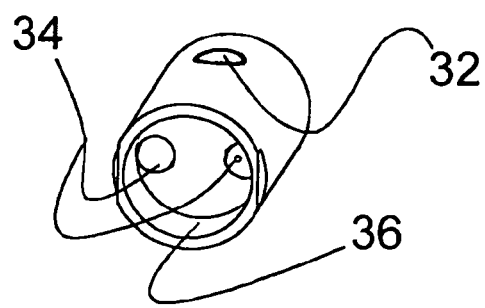
FIG. 3 is a perspective view into the interior of the cover.

As shown in FIG. 3, magnets 34, with which cover 26 can be secured on insert 12, can advantageously be provided for this purpose. A cavity 36, in which the sample, clamped between clamping jaws 18 and 20, can be received, is provided on the side of cover 26 facing toward insert 12. The sample is thus not damaged by the attachment of cover 26. The device already shown in FIG. 2 for attaching a manipulation aid 32 makes it possible to provide manipulation aids on cover 26. These serve to make possible manipulation during the mounting and removal of insert 12. In addition, these manipulation aids can, for example, be threaded by means of a thread into the refrigerated chamber of the ultramicrotome.

Figure 4:
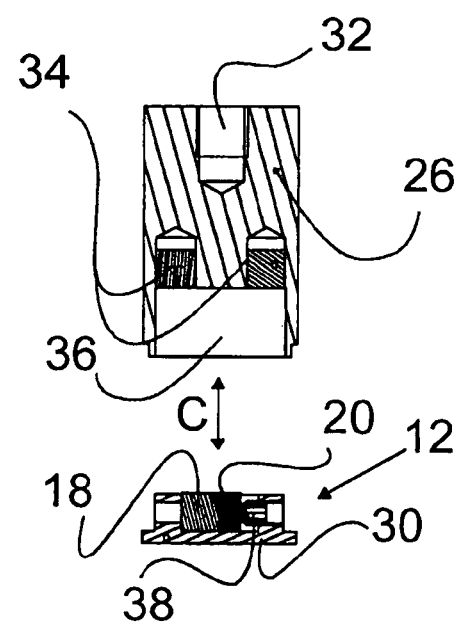
FIG. 4 shows a cross section through a cover and an insert.

FIG. 4 shows a cross section through the cover already shown in FIG. 2, and through insert 12. Using magnets 34, the cover is placed onto rim 30 of insert 12 and secured there. A sample is secured between clamping jaws 18 and 20, in which context the clamping jaws can be pushed toward one another by a clamping thread joint 38. This guarantees secure retention of the specimens between the clamping jaws. For most applications, the samples should protrude only approximately 0.3 mm out of the clamping jaws so that sufficient stability for cutting is ensured. Cavity 36 inside cover 26 must correspondingly also be dimensioned so as to rule out any contact between the specimens and insert 12.

Cover 26 is particularly suitable for transporting insert 12 from the cutting device, i.e. the microtome or ultramicrotome, to the AFM. In addition to secure transport of the sample, it is also possible in this context to ensure that transport out of a refrigerated chamber of the ultramicrotome occurs without undesirable side effects, for example condensation of water onto the sample.

Using the specimen holder according to the present invention, it is thus possible to process a sample in a cutting device, in particular in a microtome or ultramicrotome. The surface of the specimen can be cut smoothly, and thus optimally prepared for subsequent examination using an AFM. After the surface of the specimen is cut, the specimen can be removed from the cutting device together with insert 12 and arranged, with no change in position, in an AFM. It is thus easily possible to align the surface of the prepared sample perpendicular to the examining tip of the AFM.

What is claimed is:

1. A specimen holder for a microtome or ultramicrotome, comprising an insert for holding a specimen, a base element, a receiving ring for a releasable reception of the insert, the receiving ring being releasably connected to the base element, the receiving ring comprising a slot for the reception of the insert, and the insert comprising a screw and a cavity, wherein the first and second clamping jaws are disposed in the cavity, the screw is displaceable to contact one of the jaws, and the contacted jaw is displaceable within the cavity, through contact with the screw, for clamping the specimen between the jaws, wherein the specimen holder is connectable to the microtome or ultramicrotome without the use of fasteners, wherein the specimen holder is removable from the microtome or ultramicrotome for insertion in an atomic force microscope, and wherein the insert is slidingly displaceable through the slot for insertion in and removal from the slot.

2. The specimen holder as defined in claim 1, wherein the receiving ring is embodied as a screw-on ring and can be thread-joined to the base element so that the insert is clamped in the screw-on ring.

3. The specimen holder as defined in claim 1, further comprising a cover provided for removing the insert from the receiving ring.

4. The specimen holder as defined in claim 3, wherein the cover or the insert has at least one securing element for securing the cover on the insert.

5. The specimen holder as defined in claim 4, wherein the at least one securing element is a magnet.

6. The specimen holder as defined in claim 5, wherein the at least one magnet is mounted on the cover.

7. The specimen holder as defined in claim 3, wherein the cover comprises a cavity, in particular a recess, which is embodied so that the specimen is received therein.

8. The specimen holder as defined in claim 1, further comprising a cover and wherein a device for attaching a manipulation aid, for manipulation of the insert upon mounting and removal, is provided in the cover.

9. The specimen holder as defined in claim 8, wherein the device for attaching the manipulation aid is embodied as a thread.

10. A specimen holder for a microtome or ultramicrotome, comprising:

an insert with first and second displaceable clamping jaws for holding a specimen;

a receiving ring with:
- an outer circumferential surface;
- first and second oppositely disposed end surfaces; and,
- a through bore connecting the first and second end surfaces;

a slot in the receiving ring for holding the insert, the slot including a first opening at the through bore;

a lip in the receiving ring for the slot;

a second opening for the slot in the outer circumferential edge; and, a base element releasably connectable to the receiving ring.

* * * * *